US011185689B2

(12) United States Patent
Yakoub et al.

(10) Patent No.: US 11,185,689 B2
(45) Date of Patent: Nov. 30, 2021

(54) SKIN TREATMENT DEVICE AND METHOD FOR PRODUCING SAID SKIN TREATMENT DEVICE

(71) Applicant: FEELIGREEN SA, Valbonne (FR)

(72) Inventors: Abdelwahhab Yakoub, Antibes (FR); Christophe Bianchi, Nice (FR)

(73) Assignee: FEELIGREEN SA, Valbonne (FR)

( * ) Notice: Subject to any disclaimer, the term of this patent is extended or adjusted under 35 U.S.C. 154(b) by 23 days.

(21) Appl. No.: 16/308,322

(22) PCT Filed: Jun. 8, 2017

(86) PCT No.: PCT/IB2017/000920
§ 371 (c)(1),
(2) Date: Dec. 7, 2018

(87) PCT Pub. No.: WO2017/212343
PCT Pub. Date: Dec. 14, 2017

(65) Prior Publication Data
US 2019/0209836 A1    Jul. 11, 2019

(30) Foreign Application Priority Data
Jun. 8, 2016  (GB) .................................... 1610019

(51) Int. Cl.
*A61N 1/32* (2006.01)
*A61N 1/04* (2006.01)

(52) U.S. Cl.
CPC ........... *A61N 1/328* (2013.01); *A61N 1/0496* (2013.01)

(58) Field of Classification Search
CPC .............................. A61N 1/328; A61N 1/0496
See application file for complete search history.

(56) References Cited

U.S. PATENT DOCUMENTS

| 2004/0267169 | A1  | 12/2004 | Sun et al. |
| 2005/0010161 | A1* | 1/2005  | Sun ...................... A61N 1/0492 604/20 |
| 2012/0136414 | A1  | 5/2012  | Ionita-Manzatu et al. |
| 2014/0276247 | A1  | 9/2014  | Hall et al. |
| 2017/0106188 | A1* | 4/2017  | King ..................... A61N 1/328 |

FOREIGN PATENT DOCUMENTS

| CA | 2 838 411 A1 | 1/2005 |
| WO | WO 2005/004981 A2 | 1/2005 |
| WO | WO 2010/147701 A2 | 12/2010 |

OTHER PUBLICATIONS

International Search Report as issued in International Patent Application No. PCT/IB2017/000920, dated Oct. 12, 2017.

\* cited by examiner

*Primary Examiner* — Joseph M Dietrich
(74) *Attorney, Agent, or Firm* — Pillsbury Winthrop Shaw Pittman LLP

(57) ABSTRACT

A skin treatment device includes a substrate and a plurality of discrete galvanic couples provided on the substrate, each discrete galvanic couple including a first conductive electrode that is an anode and a second conductive electrode that is a cathode, wherein the anode of each galvanic couple includes a first metal and the cathode of each discrete galvanic couple includes a second metal, different from the first metal, the first and second metal having a different standard potential.

19 Claims, 4 Drawing Sheets

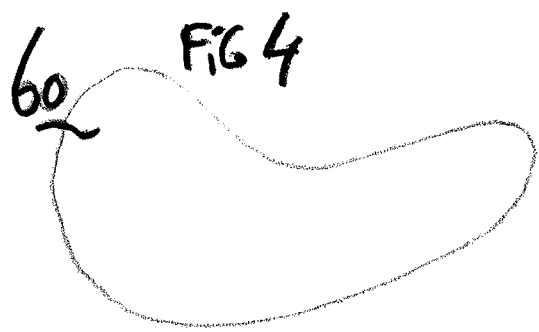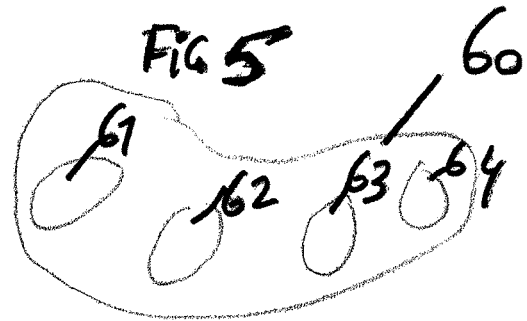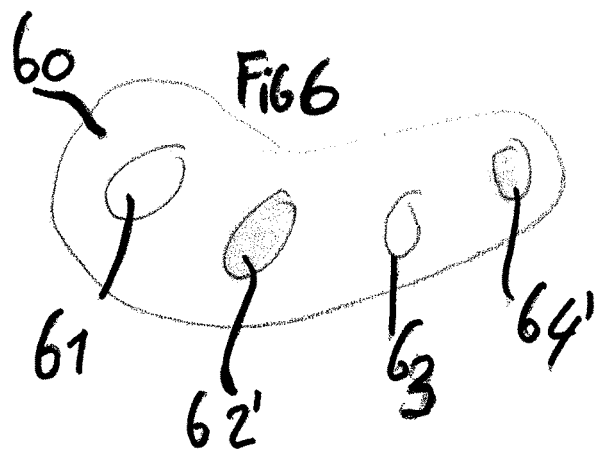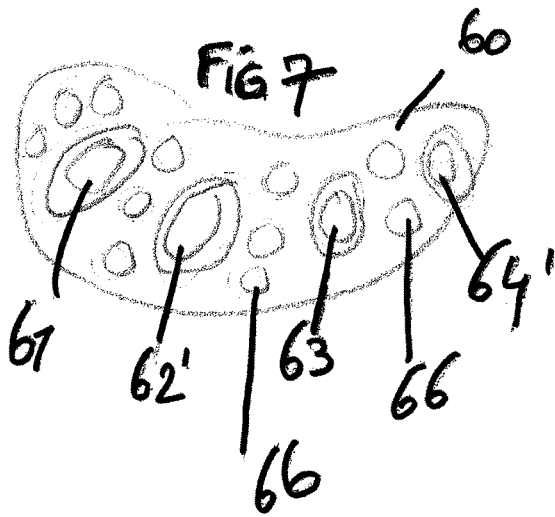

SKIN TREATMENT DEVICE AND METHOD FOR PRODUCING SAID SKIN TREATMENT DEVICE

CROSS-REFERENCE TO RELATED APPLICATIONS

This application is the U.S. National Stage of International Application Serial No. PCT/IB2017/000920, filed Jun. 8, 2017, which in turn claims priority to Great Britain Application No. 1610019.0, filed Jun. 8, 2016. The contents of all of these applications are incorporated herein by reference in their entirety.

TECHNICAL FIELD

The invention relates to a skin treatment device comprising a plurality of galvanic couples. The skin treatment device is particularly adapted to be used as a topical or cosmetic system adapted to create micro-currents to treat the skin of mammal.

BACKGROUND OF THE INVENTION

In the prior art it is known to use galvanic couples as the power source in devices for skin treatment, such as iontophoresis devices. The use of galvanic couples is, for instance, disclosed in the patent application publication US 2012/0136414 and the International Patent Application WO 2005/004981.

It is known that materials that are particularly adapted to create a galvanic couple include a zinc donor electrode and a silver chloride counter electrode. Such a combination is capable of producing an electric current of about 40 µA when the skin or conductive fluids are used to form a complete circuit with the system to generate the electricity.

A disadvantage related with the known devices is the fact that the micro-currents obtained by means of galvanic couples are relatively low. Thus, the skin treatment based on such micro-currents does not operate in an efficient manner.

It appears that there is a need to improve a topical or cosmetic system adapted to create micro-currents of about 70-100 µA, preferably 80-100 µA, whereby the topical of cosmetic is shaped to provide the micro-currents at selected areas of the skin.

OBJECT OF THE INVENTION

According to the present invention the topical or cosmetic systems have been improved to comprise a plurality of galvanic couples that comprise electrodes adapted, in use of the device, to be in communication with one another on a substrate. The galvanic couples are positioned on the substrate and are detached from each other, wherein the galvanic couples are of variable shape.

The use of a plurality of galvanic couples on the substrate enables a tailored and controlled distribution of multiple positive and negative poles over a treatment area and consequently a tailored and controlled electricity distribution to the tissue under treatment.

SUMMARY OF THE INVENTION

According to a first aspect of the invention, the invention provides a device comprising a substrate and a plurality of discrete galvanic couples provided on said substrate, each discrete galvanic couple comprising a first conductive electrode that is an anode and a second conductive electrode that is a cathode, wherein the anode of each galvanic couple comprises a first metal and the cathode of each discrete galvanic couple comprises a second metal, different from the first metal, the first and second metal having a different standard potential, characterised in that, at least one discrete galvanic couple comprises an anode having an assembly of a bottom layer connected to said substrate, said bottom layer comprising said second metal and a top layer connected to said bottom layer, said top layer comprising said first metal.

The applicants have noted that surprisingly, by using a galvanic couple with a cathode comprising a second metal and an anode having an assembly of a conductive bottom layer and a top layer comprising a first metal, the first and second metal having a different standard potential, allows for the generation of micro-currents about 70-100 µA.

According to the invention, the top layer has a surface area larger than the surface area of the bottom layer to completely cover and surround said bottom layer.

According to the invention, the first metal comprises zinc, the second metal comprises a silver halide.

According to the invention, the second metal is silver chloride.

According to the invention, the substrate comprises a flexible plastic material.

According to the invention, the substrate comprises a material selected from a PET film or a polyurethane (PU) film.

According to the invention, the substrate has a thickness of 40-80 µm, preferably 40-60 µm, with more preference 50 µm.

According to the invention, each of the anodes and the cathodes of said plurality of discrete galvanic couples is covered with a layer of a conductive adhesive material adapted to connect the skin treatment device to the skin.

According to the invention, the skin treatment device comprises an additional adhesive layer in the vicinity of at least one of the galvanic couples to improve the contact of the skin treatment device with the skin in the vicinity of said at least one of the discrete galvanic couples.

According to the invention, the skin treatment device comprises a removable protective film connected to the layer of a conductive adhesive material, the removable protective film being adapted to cover and protect the skin treatment device prior to use.

According to the invention, the first metal and the second metal comprise a conductive ink, said conductive ink being adapted for forming a metal layer on the substrate.

According to a second aspect of the invention, the invention relates to a method for producing a skin treatment device comprising the following steps:

providing a substrate, providing a plurality of discrete galvanic couples on said substrate, each discrete galvanic couple comprising a first conductive electrode that is an anode and a second conductive electrode that is a cathode, wherein the anode of each discrete galvanic couple comprises a first metal and the cathode of each discrete galvanic couple comprises a second metal, different from the first metal, the first and second metal having a different standard potential, wherein the step of providing a plurality of discrete galvanic couples comprises:

providing a plurality of discrete metal elements on the substrate, said plurality of discrete metal elements comprising a layer of said second metal, selecting discrete metal elements of the plurality of discrete metal elements, and providing a layer of said first metal on selected discrete elements to form at least one discrete galvanic couple comprising an anode having an assembly of a bottom layer comprising said second metal and a top layer comprising said first metal and a cathode having a layer comprising said second metal.

According to the invention, the step of providing a plurality of discrete metal elements on the substrate comprises:

selecting a conductive ink comprising said second metal, and printing said selected conductive ink comprising said second metal on said substrate.

According to the invention, said step of providing a layer of said first metal on selected discrete metal elements, comprises:

selecting a conductive ink comprising said first metal, and printing said selected conductive ink comprising said first metal on said at least one selected discrete metal element.

According to the invention, the method comprises:

providing on said anodes and cathodes of said plurality of discrete galvanic couples a layer of a conductive adhesive material.

BRIEF DESCRIPTION OF THE DRAWINGS

The features and advantages of the present invention will be apparent from the detailed description of exemplary embodiments of the invention, making reference to the drawings, wherein:

FIGS. 4-7 show galvanic couples at different steps of the production, said galvanic couples being adapted for the skin treatment devices according FIG. 1 or FIG. 2.

DETAILED DESCRIPTION OF THE INVENTION

Figure 1:
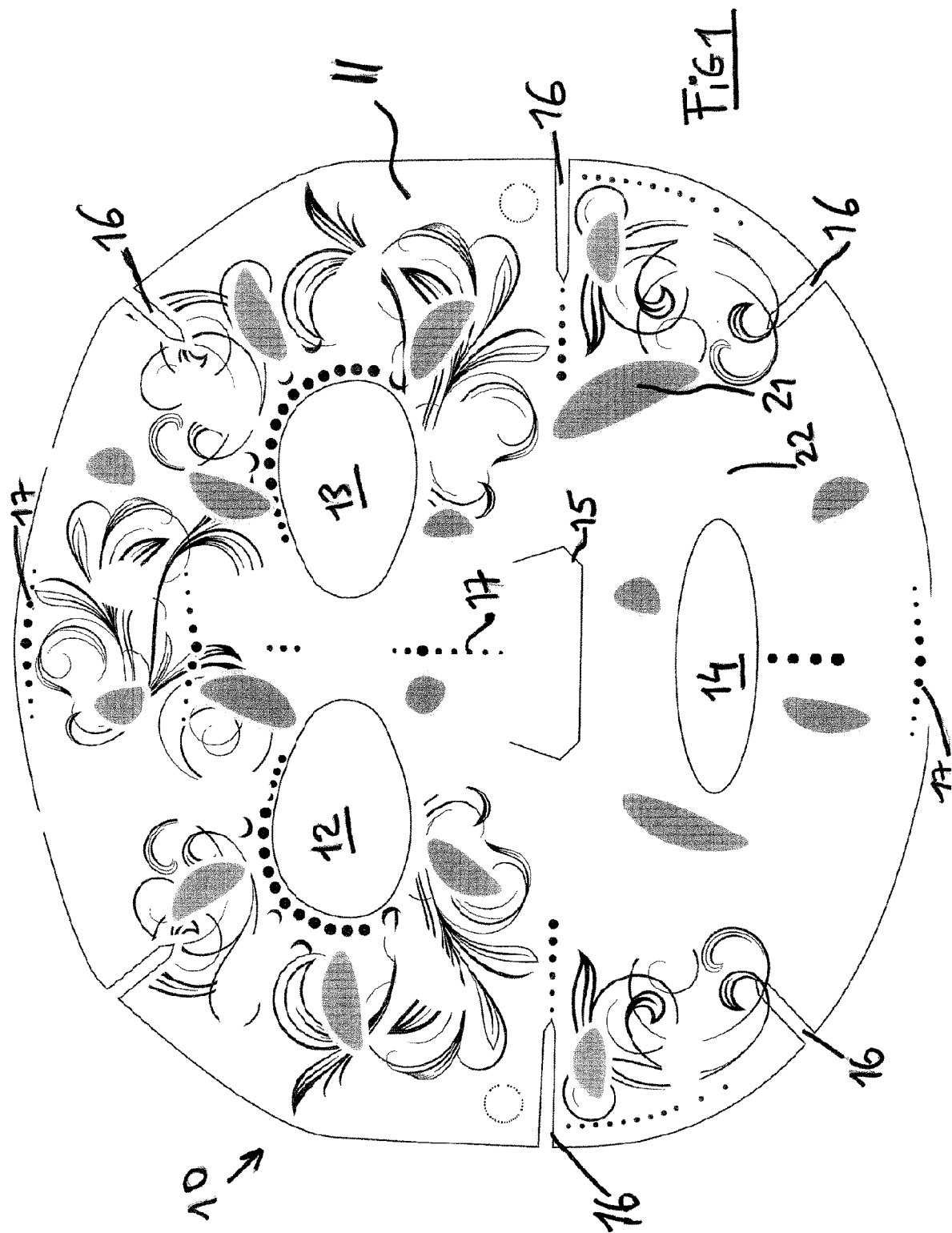
FIG. 1 shows a skin treatment device according to a first embodiment of the invention.

The invention will be described below in more detail, with reference to the accompanying drawings. It should be noted that the description of the embodiments of the invention should be construed as being merely illustrative.

For the description of the invention, all technical and scientific terms used herein have the same meaning as commonly understood by a skilled person.

The invention is described herein with respect to the treatment of skin, such as a human skin. It should be noted that the word skin makes reference to any human or animal barrier membrane including the skin or eye, oral, buccal, nasal, vaginal, gastrointestinal, or rectal mucosa.

Reference is made to a device for the treatment of the skin. The word "device" is meant to include the apparatus used for skin treatment as such or in a finished and packaged form. The device can contain a manual or instructions directing the user to apply the device to the human skin. Such instructions may be printed on the device or may be available on any additional packaging element.

The device is specifically adapted to treat the skin by using delivery of electricity to the skin and to thereby induce a desirable biological response of the tissue to which the electricity is delivered.

The present device comprises a substrate comprising a plurality of discrete galvanic couples, each galvanic couple comprising a first conductive electrode that is an anode and a second conductive electrode that is a cathode. As used herein, the generation of electricity means that free electrons can pass through the skin to which the device is applied between the first and second conductive electrodes.

In one embodiment, the skin treatment device according to the invention is a skin treatment patch, which may be placed directly against the skin.

Examples of materials that provide galvanic couples include, but are not limited to: zinc-silver, zinc-silver oxide, zinc-silver halide, zinc-silver chloride, zinc-silver bromide, zinc-silver iodide and zinc-silver fluoride.

The conductive electrodes may be applied to the substrate by means of any adapted deposition technique known in the art. For example, one or both of the first and second conductive electrodes may be a piece of metal sheet, wire or mesh, or a metal-coated fabric or other material such as a fabric coated with a metal, and its oxide, halide, and sulphide.

Alternatively, the first and second conductive electrodes may be deposited on the substrate by using chemical or electrochemical deposition such as electroless plating for chemical deposition and electroplating for electrochemical deposition as known in the art. The first and second conductive electrodes may also be deposited on the substrate by physical deposition, such as screen printing, spray coating, gravure printing, laser jet printing, pad printing, needle printing, dip coating, vacuum deposition, or other printing or transfer processes.

According to a preferred embodiment of the invention, the conductive electrodes may be created by formulating galvanic materials into inks specific to the process by which the materials are deposited, such as screen printing ink for screen printing or laser jet printing ink for laser jet printing, and may contain ingredients such as solvents, binders, or plasticizers. Care should be taken that these formulations are pharmaceutically acceptable upon drying. This means that all non-volatile ingredients must be safe for contact with the skin or any other barrier membrane.

Binders used in such inks may include those which are water soluble and water insoluble. Examples of pharmaceutically accepted binders include but are not limited to polyethylene, polypropylene, polyvinylchloride, polystyrene, acrylonitrile butadiene styrene, polyethylene terephthalate and polyurethane.

The size of the galvanic couples used in the skin treatment device according to the invention may depend on the specific application of the device. In one embodiment, adapted for cosmetic use of the skin treatment device, a galvanic couple occupies typically a surface area no greater than about 4 $cm^2$. In order to be adapted to be used, for instance on the face of a human being, the metal elements forming the galvanic couple typically have forms which are other than square. The shapes may have the form of ovals, or other forms to fit the specific surface areas of the skin to which the device is applied.

In a further embodiment each galvanic couple occupies an area no greater than about 2 $cm^2$, for example no greater then 1 $cm^2$. The overall dimensions of each galvanic couple may vary from about 0.01 $cm^2$ to about 10 $cm^2$.

In yet another embodiment, specifically adapted for the treatment of pain, the surface areas occupied by the conductive electrodes may be larger to be in the region of 10-200 $cm^2$.

The galvanic couples may be arranged in many ways, provided they are discrete from one another, that is, the individual galvanic couples are disconnected and do not touch one another. The galvanic couples can be arranged as desired to increase or decrease the density of electricity.

The galvanic couples may be arranged on the substrate to suit an intended use of the device. It is possible to use a single galvanic couple or a plurality of galvanic couples.

In practise the galvanic couples are distributed over the surface area of the substrate to obtain a tailored distribution of multiple positive and negative poles over a treatment area. As each galvanic couple acts independently of the adjacent galvanic couples, each individual couple treats the skin in the direct vicinity of the galvanic couple. This means that, on a substrate, the size of the galvanic couples can be adapted and selected to control the level of electricity produced.

The skin treatment device according to the invention comprises a substrate, on which the galvanic couples are fixed. This substrate may be fabricated into various shapes and sizes to fit the contours of various anatomical surfaces of the skin or other barrier membranes. For example, the substrate may have a shape and form adapted to cover a large surface area of a human face. This means that the substrate has the shape of a facial mask with openings to expose at least the eyes and mouth. The skin treatment device could also have the shape of a single or a plurality of partial facial masks, each adapted to only cover part of the face.

The substrate may be made of a variety of materials, such as paper, plastic or water-insoluble polymer, woven materials (e.g. woven fabric), and non-woven materials (nonwoven fabric). The substrate may comprise "breathable" material such as, but not limited to, a cotton or synthetic woven and nonwoven fabric layer, such as those fabric materials commonly used for bandages and sports bandages. The substrate may comprise electrically conductive material, such as electrically conductive plastic, woven, nonwoven, or paper.

In a preferred embodiment, the substrate comprises a PET film or a Polyurethane film.

The skin treatment device comprises an adhesive layer such as an adhesive polymeric layer, to connect the device against the skin of a user. This adhesive layer is present at each of the galvanic couples to allow the conductive electrodes of the galvanic couples to be in contact with the skin.

It is possible to provide the substrate with additional adhesive material, in particular adjacent to the galvanic couples to further improve the contact with the human skin.

The skin treatment device according to the invention may comprise a removable release liner, to cover the substrate and in particular to cover the adhesive material, prior to use of the device. The release liner is typically a polymer sheet or a paper or fabric coated with a polymer, which has weak adhesion towards the adhesive material used, thereby allowing it to be easily removed prior to use without damaging the skin treatment device. Examples of the polymers typically used for the release liner are silicones and polyethylenes.

In addition to, or in lieu of, the use of an adhesive, the skin treatment device may be fastened to the skin with an adhesive tape, an elastic band or any other adapted material. Optionally, the skin treatment device according to the invention could be used together with a facial mask, wherein the skin treatment device is positioned between the skin of a user on one side and the interior of the facial mask on the other side.

The skin treatment device according to the invention induces certain desirable biological responses that facilitate the treatment of the skin conditions. These desirable biological responses may be induced by the electric current passage through the skin. Examples of the desirable responses of the skin may include, but are not limited to rejuvenation of the skin by stimulating collagen, inhibition of anaerobotic microbial growth and establishment of a healthier membrane microflora or, blood vasoconstriction and enhanced tissue immunological activity, improved tissue repairing.

In one embodiment, the skin treatment device is used to eliminate or reduce various types of pain or other sensory discomfort, including but not limited to, back pain, joint pain, neck pain, shoulder pain, tingling or numbness of the skin, post-surgical pain, muscle soreness, muscle cramps, menstrual cramps, joint stiffness, headache or stomach pain. When used for the pain of deeper tissues or organs other than the skin, the electrodes of the galvanic couples are larger in size and spaced farther apart in order to deliver electric stimulation deeper and to cover larger areas of the body, for example in treating back pain, knee pain, shoulder pain or neck pain.

In a preferred embodiment, the skin treatment device is configured as a booster patch that may be applied directly to the skin.

In FIG. 1 a first exemplary embodiment of the skin treatment device 10 according to the invention is shown. The skin treatment device 10 according to FIG. 1 has the form of a patch which is adapted to be used as a facial mask. The size and the shape of the skin treatment device 10 are adapted for allowing the use of the skin treatment device 10 by a large variety of users.

The skin treatment device 10 comprises a substrate 11 on which a plurality of galvanic couples are provided. The substrate 11 comprises, for instance, a PET film or a Polyurethane film. The thickness of the substrate 11 is in the order of 50 µm. The combination of the selected material for the substrate 11 and the thickness of said substrate 11, allows the substrate 11 to be sufficiently flexible to be connected to a curved surface, such as the skin face of a user.

The substrate 11 of the skin treatment device 10 comprises a first 12 and a second 13 aperture to allow the eyes of a user not to be covered during use of the skin treatment device 10. The substrate 11 further comprises a third aperture 14 to avoid the mouth of a user to be covered during the use of the skin treatment device.

The substrate 11 further comprises a cutting line 15 which has the form of the lower part of the human nose. The cutting line 15 allows the positioning of the substrate 11 around the bottom part of the nose of a user.

The circumference of the substrate 11 is provided with a number of indentations 16. These indentations 16 are adapted to partially fold the substrate 11 to thereby improve the contact of the substrate 11 with the skin of a user.

The substrate 11 is further provided with markings 17. According to the embodiment of FIG. 1, the markings 17 have the form of dotted lines. These markings 17 can be used by a user to correctly position the skin treatment device 10 on the face.

In order to allow skin treatment, the skin treatment device 10 comprises a plurality of discrete galvanic couples. Each galvanic couple comprises a first conductive electrode that is an anode and a second conductive electrode that is a cathode.

In FIG. 1, the anodes have a darker colour than the cathodes. Each of the anodes and cathodes for the galvanic couples has similar shape and size. For clarity reasons not all galvanic couples of the skin treatment device 10 are referenced by means of reference numbers. Reference is made to one galvanic couple only, comprising an anode 21 and a cathode 22.

With reference to FIG. 3 and FIGS. 4-7, the anode 21 comprises an assembly of a conductive bottom layer which is fixed on the substrate 11. In the embodiment according to FIG. 1, the conductive bottom layer comprises silver chloride. The anode 21 further comprises a metal top layer, which covers the conductive bottom layer. In the example of FIG. 1, the top layer comprises zinc. The cathode 22 comprises a layer of silver chloride.

Both the anode 21 and the cathode 22 are covered by means of a conductive adhesive to allow the connection of the skin treatment device 10 to the skin of a user.

The first metal forming the top layer of the anode and second metal forming the cathode of each galvanic couple are selected to have a different standard potential. In use, the skin provides conductivity between the anode and the cathode, thereby allowing a micro current to flow through the skin. In case of using zinc as the first metal to form the anode and silver chloride as the second metal to form the cathode, a micro current of about 40 µA can be produced.

Surprisingly, by adding a conductive bottom layer between the first metal and substrate 11 the efficiency of the galvanic couple is improved. When using zinc as the first metal to form the anode and silver chloride as the second metal to form the cathode, whereby the bottom layer of the anode is formed by silver chloride, a micro current in the region of 70-100 µA can be produced.

Figure 2:
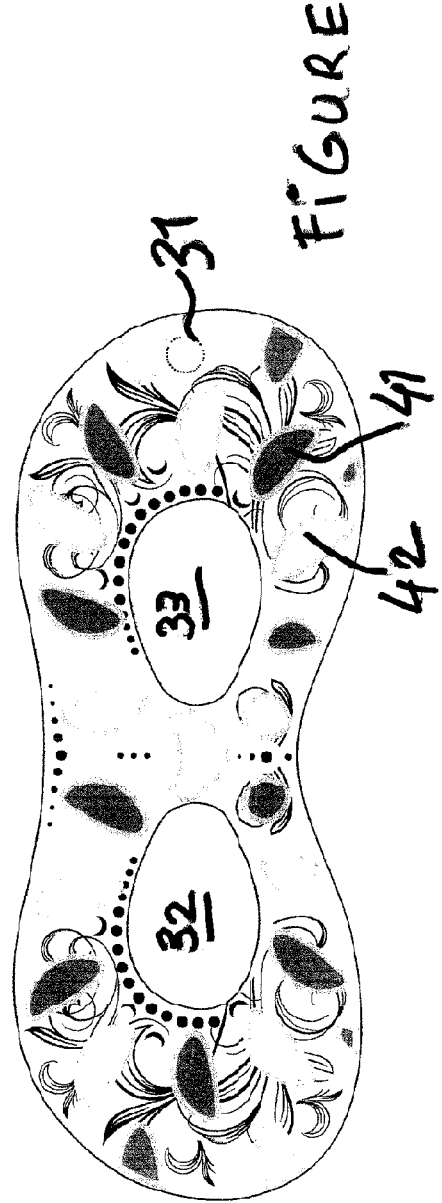
FIG. 2 shows a skin treatment device according to a second embodiment of the invention.

In FIG. 2 a second exemplary embodiment of the skin treatment device 30 according to the invention is shown. The skin treatment device 30 according to FIG. 2 has the form of a patch which is adapted to be used as a mask to cover the area of the face adjacent to the eyes. The size and the shape of the skin treatment device 30 are adapted for allowing the use of the skin treatment device 30 by a large variety of users.

The skin treatment device 30 comprises a substrate 31 on which substrate 31 a plurality of galvanic couples are provided. The substrate 31 comprises, for instance, a PET film or a Polyurethane film. The thickness of the substrate 31 is in the region of 50 µm. The combination of the selected material for the substrate 11 and the thickness of said substrate 31, allows the substrate 31 to be sufficiently flexible to be connected to a curved surface, such as the skin face of a user.

The substrate 31 of the skin treatment device 30 comprises a first 32 and a second 33 aperture to allow the eyes of a user not to be covered during use of the skin treatment device 30.

In order to allow skin treatment, the skin treatment device 30 comprises a plurality of galvanic couples. Each galvanic couple comprises a first conductive electrode that is an anode and a second conductive electrode that is a cathode.

In FIG. 2 the anodes have a darker colour than the cathodes. Each of the anodes and cathodes for the galvanic couples has similar shape and size. For clarity reasons not all galvanic couples are referenced by means of reference numbers. Reference is made to one galvanic couple only, comprising an anode 41 and a cathode 42.

With reference to FIG. 3 and FIGS. 4-7, the anode 41 comprises an assembly of a conductive bottom layer which is fixed on the substrate 31. In the embodiment according to FIG. 2, the conductive bottom layer comprises silver chloride. The anode 41 further comprises a metal top layer, which covers the conductive bottom layer. In the example of FIG. 1, the top layer comprises zinc. The cathode 42 comprises a layer of silver chloride.

Figure 3:
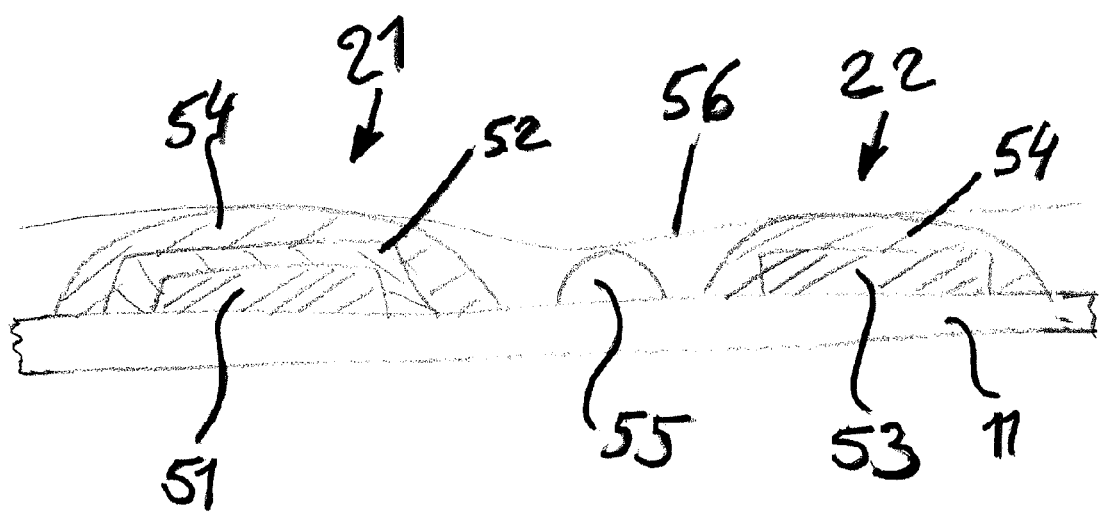
FIG. 3 shows a galvanic couple of the skin treatment device according to FIG. 1 or FIG. 2 in cross section.

In FIG. 3, schematically, a galvanic couple for the skin treatment device 10 according to the invention is shown in cross section. The skin treatment device 30 comprises the same type of galvanic couples.

The galvanic couple according to FIG. 3 comprises an anode 21 and a cathode 22, both fixed on top of the substrate 11. The anode 21 comprises a conductive bottom layer 51. In the example of FIG. 3, the bottom layer 51 comprises silver chloride. The bottom layer 51 is fixed on the substrate 11. The anode 21 further comprises a top layer 52, which comprises zinc. The top layer 52 is formed to completely cover the bottom layer 51. The cathode 22 comprises a single layer 53, which comprises silver chloride.

Both the anode 21 and the cathode 22 are covered by means of a layer 54 comprising conductive adhesive material to allow the connection of the skin treatment device 10 and in particular the anode 21 and the cathode 22 to the skin of a user.

To further improve the connection of the galvanic couple 21, 22 to the skin of a user, a further adhesive element 55 comprising said conductive adhesive can be added to the substrate 11. The presence of the additional element 55 enhances the contact between the galvanic couple 21, 22 and the skin.

As shown in FIG. 3, the adhesive material can be protected by using releasable liner 56 prior to use of the skin treatment device 10. This liner 56 is adapted to have a limited adhesion with the adhesive layers 55 and 56 on the substrate 11.

In FIGS. 4-7, different steps of an exemplary embodiment of a method for producing a skin treatment device according to the invention are described.

In FIG. 4, a substrate 60 which forms the basis of the skin treatment device is shown. According to a preferred embodiment of the method for producing a skin treatment device, the substrate 60 is selected to comprise a PET film or Polyurethane film.

As shown in FIG. 5, in a first step of the production process, four discrete metal elements 61, 62, 63, 64 are fixed on the substrate 60. According to the invention, the step of fixing the four discrete metal elements 61, 62, 63, 64 on the substrate comprises selecting a conductive ink comprising a second metal, the second metal being adapted for forming the cathode of a galvanic couple and for printing the conductive ink on the substrate. According to the invention, the conductive ink for screen printing the four discrete metal elements 61, 62, 63, 64 comprises silver chloride and is adapted to be printed on the substrate 60 using screen printing.

As shown in FIG. 6, in a following step, discrete metal elements 62, 64 are both covered by means of a first metal, adapted to form an anode. According to the invention, the step of covering the discrete metal elements 62, 64 by means of a first metal comprises selecting a conductive ink comprising a first metal, the first metal being adapted for forming the anode of a galvanic couple and for printing the conductive ink on the substrate. According to the invention, the conductive ink adapted for forming the anode comprises zinc and is adapted to be printed on the discrete metal elements 62, 64 by means of screen printing. Each of the formed anodes 62', 64' comprises a bottom layer comprising the second material and a top layer comprising the first material.

In FIG. 7 a further step is shown wherein the discrete metal elements 61, 62', 63, 64' are covered using an adhesive polymeric layer. According to the invention this step comprises selecting an adhesive polymeric material adapted for application using printing and printing said polymeric adhesive material on the discrete metal elements 61, 62', 63, 64'.

As shown in FIG. 7, in addition to covering the discrete metal elements 61, 62', 63, 64' by means of the polymeric adhesive material, further adhesive material in the form of elements 66 are attached to the substrate 60. These further elements 66 are used to improve the contact of the anodes and cathodes with the skin of a user when using the skin treatment device.

What is claimed is:

1. A skin treatment device comprising a substrate and a plurality of discrete galvanic couples provided on said substrate, each discrete galvanic couple comprising a first conductive electrode that is an anode and a second conductive electrode that is a cathode, wherein the anode of each galvanic couple comprises a first metal and the cathode of each discrete galvanic couple comprises a second metal, different from the first metal, the first and second metal having a different standard potential, wherein, at least one discrete galvanic couple comprises an anode that consists of an assembly of a bottom layer in contact with said substrate and a top layer, the top layer made of a first material comprising said first metal and said bottom layer made of a second material comprising said second metal, the top layer fully covering the bottom layer and in contact with the bottom layer, and the at least one discrete galvanic couple comprises a cathode that consists of a layer in contact with the substrate and made of said second material, the first and second metal of said at least one discrete galvanic couple being selected to allow a generation of a current from 70 to 100 μA between said anode and said cathode.

2. The skin treatment device according to claim 1, wherein the top layer has a surface area larger than the surface area of the bottom layer to completely cover and surround said bottom layer.

3. The skin treatment device according to claim 1, wherein said first metal comprises zinc and said second metal comprising a silver halide.

4. The skin treatment device according to claim 3, wherein said second metal is silver chloride.

5. The skin treatment device according to claim 1, wherein the substrate comprises a flexible plastic material.

6. The skin treatment device according to claim 5, wherein the substrate comprises a material selected from a PET film or a polyurethane film.

7. The skin treatment device according to claim 5, wherein the substrate has a thickness of 40-80 μm.

8. The skin treatment device according to claim 1, wherein each of the anodes and the cathodes of said plurality of discrete galvanic couples is covered with a layer of a conductive adhesive material adapted to connect the skin treatment device to the skin.

9. The skin treatment device according to claim 8, comprising an additional adhesive layer in the vicinity of at least one of the galvanic couples to improve the contact of the skin treatment device with the skin in the vicinity of said at least one of the discrete galvanic couples.

10. The skin treatment device according to claim 8, comprising a removable protective film connected to the layer of a conductive adhesive material, the removable protective film being adapted to cover and protect the skin treatment device prior to use.

11. The skin treatment device according to claim 1, wherein the first metal and the second metal comprise a conductive ink, said conductive ink being adapted for forming a metal layer on the substrate.

12. The skin treatment device according to claim 7, wherein the substrate has a thickness of 40-60 μm.

13. The skin treatment device according to claim 12, wherein the substrate has a thickness of 50 μm.

14. The skin treatment device according to claim 1, wherein the top layer is in contact with the substrate.

15. The skin treatment device according to claim 1, further comprising an adhesive layer arranged between the anode and the cathode of the at least one discrete galvanic couple, the adhesive layer being in contact with the substrate and being out of contact with the anode and the cathode of the at least one discrete galvanic couple.

16. A method for producing a skin treatment device comprising:
providing a substrate,
providing a plurality of discrete galvanic couples on said substrate, each discrete galvanic couple comprising a first conductive electrode that is an anode and a second conductive electrode that is a cathode, wherein the anode of each discrete galvanic couple comprises a first metal and the cathode of each discrete galvanic couple comprises a second metal, different from the first metal, the first and second metal having a different standard potential, wherein providing a plurality of discrete galvanic couples comprises:
providing a plurality of discrete metal elements on the substrate, said plurality of discrete metal elements comprising a layer of said second metal,
selecting discrete metal elements of the plurality of discrete metal elements, and
providing a layer of said first metal on selected discrete metal elements, wherein at least one discrete galvanic couple comprises an anode that consists of an assembly of a bottom layer in contact with said substrate and a top layer, the top layer made of a first material comprising said first metal and said bottom layer made of a second material comprising said second metal, the top layer fully covering the bottom layer and in contact with the bottom layer, and the at least one discrete galvanic couple comprises a cathode that consists of a layer in contact with the substrate and made of said second material, the first and second metal of said at least one discrete galvanic couple being selected to allow a generation of a current from 70 to 100 μA between said anode and said cathode.

17. The method according to claim 16, wherein providing a plurality of discrete metal elements on the substrate comprises:
selecting a conductive ink comprising said second metal, and
printing said selected conductive ink comprising said second metal on said substrate.

18. The method according to claim 16, wherein providing a layer of said first metal on selected discrete metal elements, comprises:
selecting a conductive ink comprising said first metal, and
printing said selected conductive ink comprising said first metal on said at least one selected discrete metal element.

19. The method according to claim 16, comprising:
providing on said anodes and cathodes of said plurality of discrete galvanic couples a layer of a conductive adhesive material.

* * * * *